United States Patent [19]
Dotter

[11] Patent Number: 5,848,027
[45] Date of Patent: Dec. 8, 1998

[54] METHOD FOR PROCESSING PERSONAL DATA

[75] Inventor: James E. Dotter, Boulder, Colo.

[73] Assignee: Biometrics, Inc., Boulder, Colo.

[21] Appl. No.: 14,330

[22] Filed: Jan. 27, 1998

Related U.S. Application Data

[63] Continuation of Ser. No. 562,016, Nov. 22, 1995, Pat. No. 5,719,825.

[51] Int. Cl.⁶ .............................. G04B 47/00; A61B 5/02
[52] U.S. Cl. ............................... 368/10; 368/11; 128/670
[58] Field of Search .............................. 368/10, 11, 107, 368/113; 128/670, 677, 690, 695, 696, 903; 364/569

[56] References Cited

U.S. PATENT DOCUMENTS

| | | | |
|---|---|---|---|
| 3,846,704 | 11/1974 | Bessette | 325/66 |
| 4,567,883 | 2/1986 | Langer et al. | 128/696 |
| 4,784,162 | 11/1988 | Ricks et al. | 128/903 |
| 5,297,231 | 3/1994 | Miller | 395/2.1 |
| 5,539,706 | 7/1996 | Takewaka | 368/12 |

*Primary Examiner*—Vit W. Miska
*Attorney, Agent, or Firm*—Dorr, Carson, Sloan & Birney, P.C.

[57] ABSTRACT

A system for recording designated physical activity during the period of activity by means of a digital timepiece carried by an athlete or user for subsequent playback after the activity via an audible transmission link to a digital computer for processing, analysis and display.

14 Claims, 3 Drawing Sheets

METHOD FOR PROCESSING PERSONAL DATA

RELATED APPLICATION

This application is a continuation of the Applicant's U.S. patent application Ser. No. 08/562,016 filed Nov. 22, 1995, entitled "Method For Processing Personal Data", now U.S. Pat. No. 5,719,825.

BACKGROUND OF THE INVENTION

1. Field of the Invention.

The invention relates generally to a personal data source that is programmable for downloading to a personal computer for storage and further processing of the data and, more particularly, but not by way of limitation, it relates to a data gathering wrist watch that is capable of transmitting stored data for download to a personal computer via audio transmission.

2. Description of the Prior Art.

The prior art includes a number of timepieces or wrist watches that have additional capabilities of data processing and storage, and such timepieces may include a plurality of ancillary timing functions that are monitored by the timepiece. A personal computer may be utilized to receive sensor data from a selected source for the purpose of further processing and/or storage of the selected data. Applicant is unaware of any prior use of a timepiece to monitor physical activity for subsequent download via audio tone to a personal computer wherein the physical activity may be further processed, stored and/or printed out.

SUMMARY OF THE INVENTION

The present invention relates to a source mechanism carried on a person's body that is programmed to store certain parameters of the person's physical characteristics, parameters and work product when under stress, isolation or other inconvenience over a predetermined time period; thereafter, the program source can be actuated to transmit audibly the stored parameter data for reception by audio input hardware in association with a personal computer that is programmed to analyze, evaluate, store, print out and the like, all of the performance or other related data gathered during the predetermined time period.

Therefore, it is an object of the present invention to provide a timepiece for recording various of the bearer's performance parameters for subsequent download and processing in a personal computer.

It is also an object of the present invention to provide a timepiece to be worn by such as a researcher through his various activities to provide reliable recording of work data for subsequent download and analysis.

It is yet further an object of the invention to provide a wrist borne timepiece that is capable of monitoring and storing athletic information such as a runner's date and time of workout, lap times, finish times, heart rate data, selected ECG data, etc.

Finally, it is an object of the present invention to provide a programmable timepiece including piezoelectric tone generator that is actuatable to download all data parameters for a pre-determined time period in audible code transmission.

Other objects and advantages of the invention will be evident from the following detailed description when read in conjunction with the accompanying drawings that illustrate the invention.

DETAILED DESCRIPTION OF THE INVENTION

Figure 1:
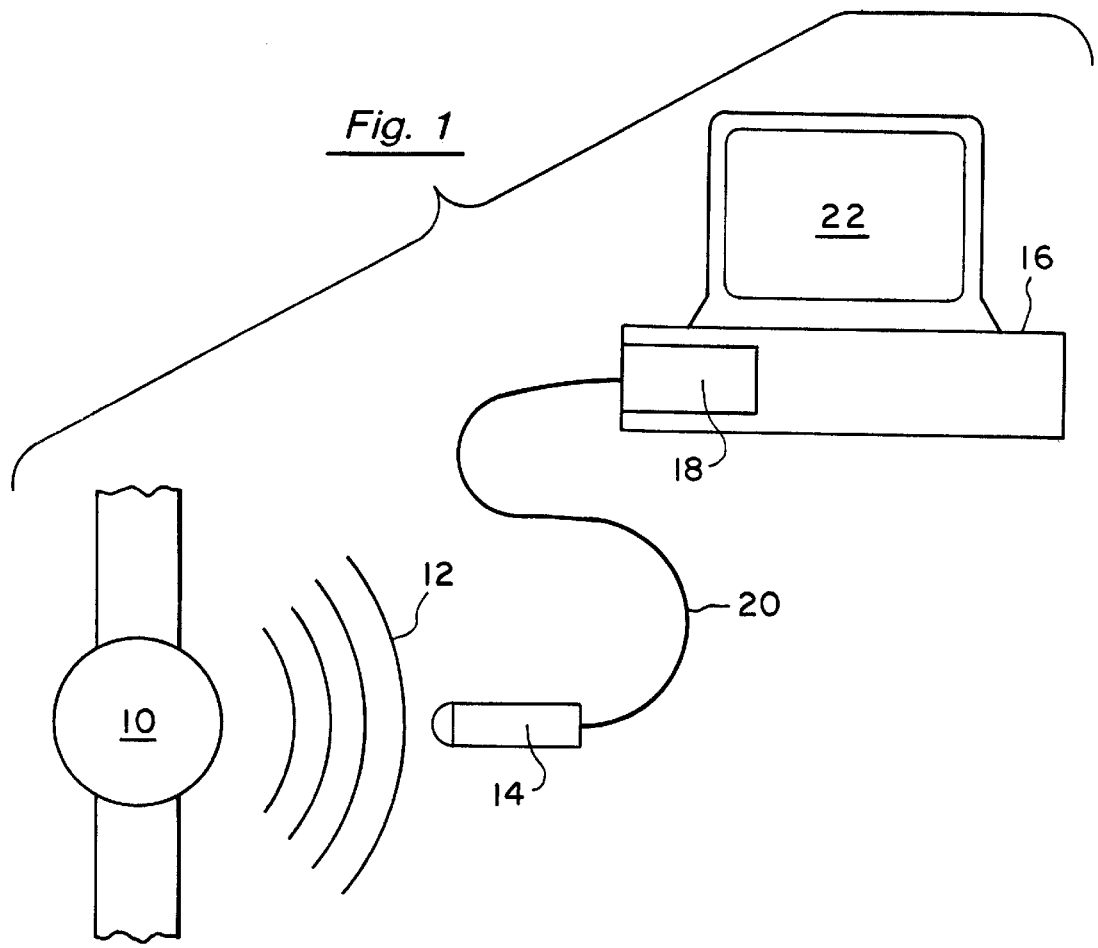
FIG. 1 is an idealized drawing of a timepiece in download proximity to a personal computer having audible input capability.

FIG. 1 illustrates the basic scheme wherein a portable source such as a timepiece 10, for example a multiple data digital wrist watch, stores selected data for subsequent readout. One form of readout would be the audible "beeps" producing audio energy 12 that is subject to pickup by a microphone 14 for input to a standard type of personal computer 16. The timepiece 10 may be any type of digital instrument that is controlled by a microprocessor and that contains a piezoelectric element for producing beep tone for signal transmission purposes. The personal computer 16, e.g., an IBM, Apple or any of many other PC computers, is equipped with the hardware package 18 connected via cable 20 to the microphone 14. The computer 16 is then capable of capturing audio energy as well as being able to reproduce sound such as music, voice or tone through external speakers. The audio hardware with audio port is sometimes built-in to the original PC equipment 16; however, it often is added in the form of a sound card or board that is compatible with the particular computer. Computer 16 may also be equipped with the output display 22.

Figure 2:
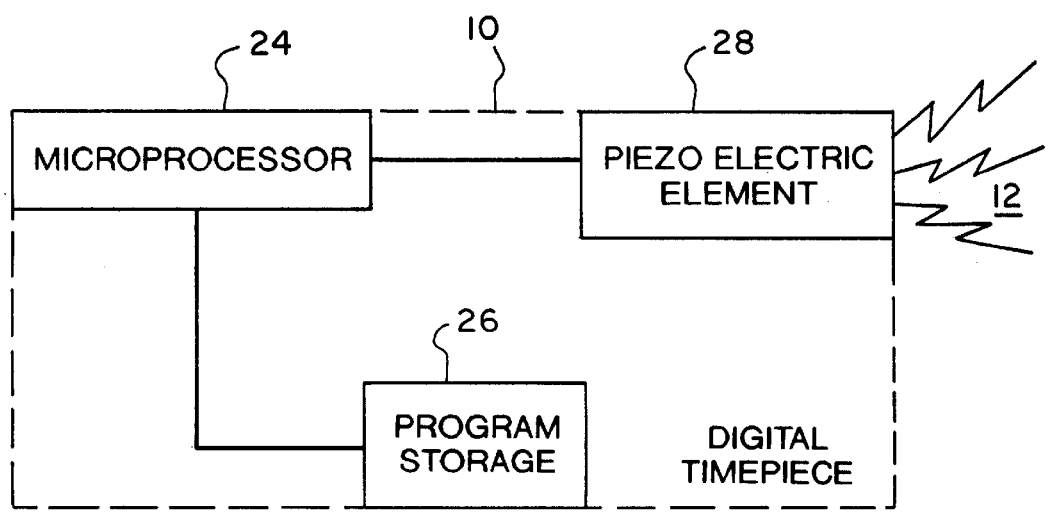
FIG. 2 is a functional block diagram of a digital timepiece having requisite program, storage and transmission elements.

The timepiece 10, as shown in FIG. 2, includes an internal microprocessor 24 that provides the basic clock count for the timepiece. The microprocessor 24 may also control a program storage 26 operating in conjunction with internal random access memory, and a piezoelectric element 28 is capable of producing selected tone output. Thus, the piezo element 28 is utilized to provide the "beep" tone such as that produced for alarms and such by most digital wrist watches. It can also be used under control of a program stored in storage 26 and operating through micro-processor 24 to transmit stored data for pickup by the microphone 14 and further processing, storage, comparison and the like within the personal computer 16.

A watch program resident in program storage 26 controls the operation of the timepiece 10. This software typically allows the user access to the features and functions of the timepiece 10 as they are controlled by the watch program and include such as setting the time, setting alarms, starting a stop watch, and maintaining a record of various data gathering, athletic or running activities of the athlete or user. The timepiece 10 is particularly useful to runners and aerobicists since the various timing functions of timepiece 10 enable storage of such as date and time of workout, lap time, finish times, and progressive heart rate data, ECG-specifics, etc. as the workout proceeds. The user can gather such information and then play it back via the audible beep transmission through microphone 14 (FIG. 1) for further processing and/or final recording and display at personal computer 16. This enables various results of the user to be compared over a longer period of time to derive progress evaluation and the like.

The present invention employs the general process of transmitting data from a wrist watch using the piezoelectric element 28, and receiving that data with a personal computer 16 that is equipped with necessary audio hardware 18 and microphone 14. A watch program in storage 26 enables the user to initiate audio data transmission, as will be further described, while the program also determines the data to be transmitted in accordance with the built-in functions that the process is being made to serve. The watch program controls the piezo element 28 and encodes data elements (databits) into the sounds produced by the piezo element 28. Many standard methods of encoding are currently used in data communications of this nature, but two primary examples of such methods are DFSK (dual frequency shift keying) modulation and CW (continuous waveform) modulation. These are well known methods: in DFSK, a high frequency tone can indicate a "1" databit while a low frequency tone indicates a "0" databit; and, in CW modulation, a tone of any fixed frequency indicates a "1" databit while silence indicates the "0" databits. The databits, whether encoded "0" or "1", are all of the same duration.

The data transmission begins with a uniform initiation sequence. This is a sequence of databits in a predetermined pattern. An example of an acceptable pattern would be "1010". Actual data may then be transmitted immediately after the initiation sequence. The actual data follows the same rules as the initialization sequence databits as far as duration and modulation schemes are concerned. There are no conditions placed on the actual content, format, or protocol of the data that is being transmitted as the watch program is constrained to send the data in the same audio format and protocol as the personal computer program functions to receive the data.

The PC program allows the user to place the personal computer 16 into a datacom receive mode wherein the microphone 14 is capturing the sound 12 emanating from the timepiece 10. The PC program allows the user to terminate the receive mode after the watch has finished transmitting. The PC program can then analyze the captured audio file and demodulate the audio sample for conversion to binary data. This is done based on a selected modulation scheme. From the pre-established initiation sequence, a determination can be made of (1) the duration of each data bit (i.e., number of samples) and (2) the specific frequency (or silence) used to indicate a "1" numeral or a "0" numeral data bit. The PC program can interpret the converted data according to the pre-established format and protocol to which the watch has been designed, and this means that both the watch and the personal computer are programmed to agree on the data format.

Figure 3:
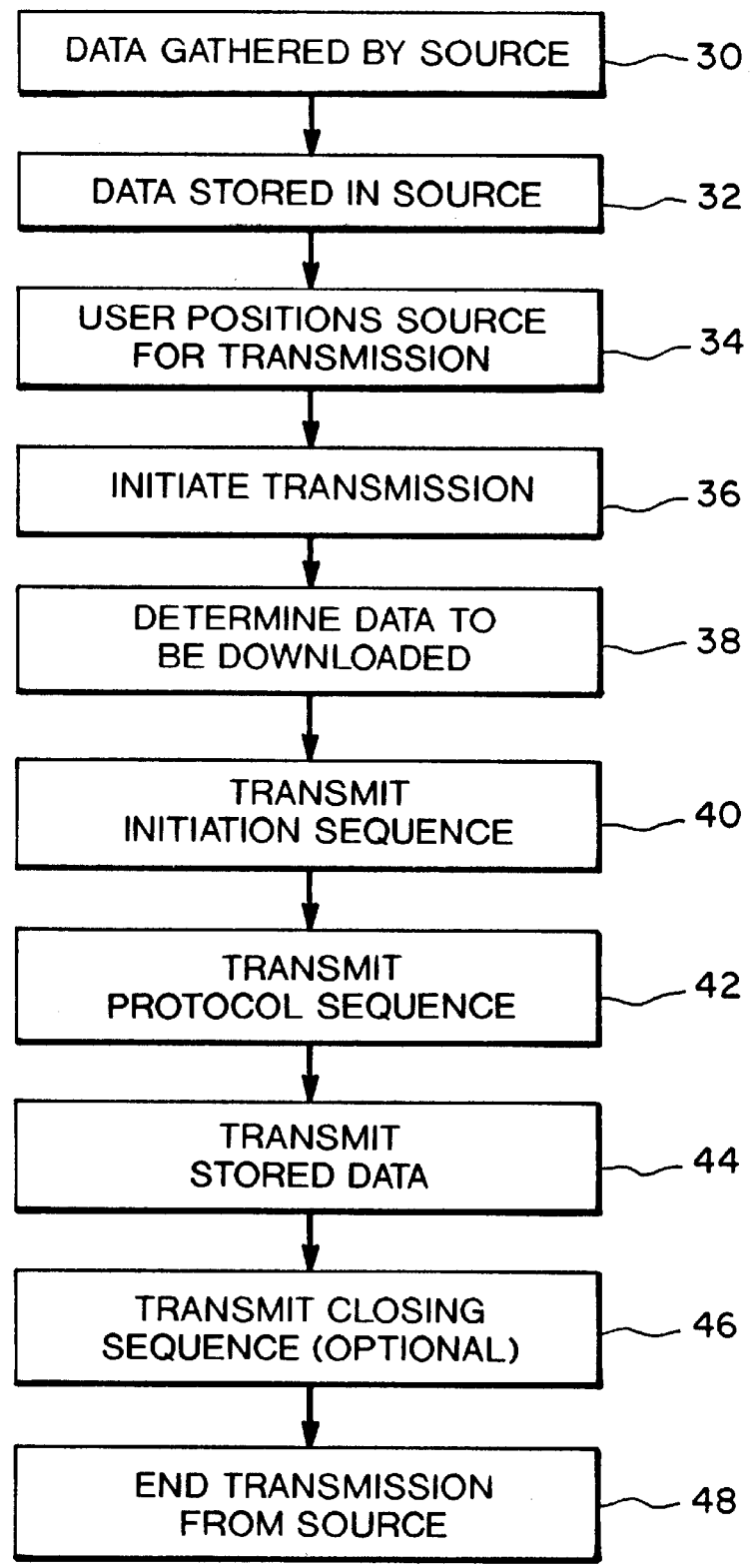
FIG. 3 is a flow diagram of the data process at the source or timepiece.

FIG. 3 illustrates the functional flow diagram for the time-piece 10 portion of the transmission system. The word "source" is used to identify the timepiece 10 or comparable element, and the broad reference is selected because in some cases the transmitter element may be a totally hybrid microprocessor-driven electronic assembly that is carried by the user and capable of a very large number of timing and physical assessments for storage and transmission. Thus, it should be understood that a "source" is the equivalent of the FIG. 2 illustration of the microprocessor-driven digital timepiece.

Referring to FIG. 3, a first flow step 30 indicates the process of data gathering by the source and, as previously stated, the source stores gathered data for further downloading. Such data may include various forms of user data relating to a particular field job or athletic workout and resulting physical effects. The data is stored in the source at flow stage 32 and, according to the type of program sequencing, such data may be stored in program storage 26 or in the microprocessor 24 internal storage (see FIG. 2). When the current task or workout is terminated, data creation ceases and the stored data in the source is ready for download at a designated location that includes audible pickup equipment 14–18 and personal computer 16 (FIG. 1).

As at flow stage 34, the user positions the source for audible transmission adjacent microphone 14 at the playback station so that the coded beeps (audio energy 12) emanate from the source or timepiece 10 into the microphone 14. Download transmission is initiated at flow stage 36 by giving a command to the timepiece or source to-commence the download function. This command may be given by the user pressing buttons on the source, or by the personal computer 16 sending instructions to the source via a PC-to-source communication channel (optional). Such command may include instructions on the specific data to be downloaded, or it may simply request that all stored data be downloaded.

Logic circuitry in the source, e.g., microprocessor 24 controlled by program storage 26, accomplishes the transmission of data as a series of "beeps" in predetermined code formation emanating from timepiece 10 or other source. As at flow stage 38 the data to be downloaded is determined and this may be based on either the command received at initiation, or the internal logic that allows the source code to determine the string of data bytes that it will transmit. In flow stage 40, the uniform initiation sequence is transmitted and this sequence is a recognizable pattern of zeros and ones that is predetermined. The sequence is anticipated by the PC program as an indication of the start of data transmission as each bit of the sequence is encoded as a tone or silence, and the source piezoelectric element is controlled to represent each bit in turn. Each bit is represented by a given state of the piezoelectric element for an equal duration of time. That is, the source sends a sequence of "11010" as four ten millisecond intervals: that is, tone on, off, on, off.

A protocol sequence may then be transmitted next as at flow stage 42. Depending on the protocol previously agreed upon by the source user and the PC program, the watch or source may next transmit bytes of data that indicate the meaning of the data to be sent, i.e., how many bytes of data to expect or other pertinent facts about the transmission. For example, with no break in the timing from the transmission of previous initiation sequence bits, the source may transmit a special byte to indicate that the transmission will consist of 27 data bytes plus one checksum byte. Thereafter, stored data is transmitted via flow stage 44 as stored data is transmitted bit-by-bit as audible tones by means of the piezoelectric element 28. Each bit of the actual data is encoded as a tone or silence, and the source piezo element 28 is controlled to represent each by a given piezoelectric state for an equal and established duration of time. Thus, with no break in the timing from transmission of previous bits, the source transmits each bit of 27 data bytes with the most significant bit first (MSB). Optionally, a closing sequence may be transmitted as at stage 46 to allow verification of transmitted data. With no break in the timing from transmission of previous bits, the source may transmit each bit of the checksum byte thereby to provide verification. Flow stage 48 ends transmission whereupon all data has been audibly transmitted and the source or timepiece is allowed to fall back into normal operating state.

Figure 4:
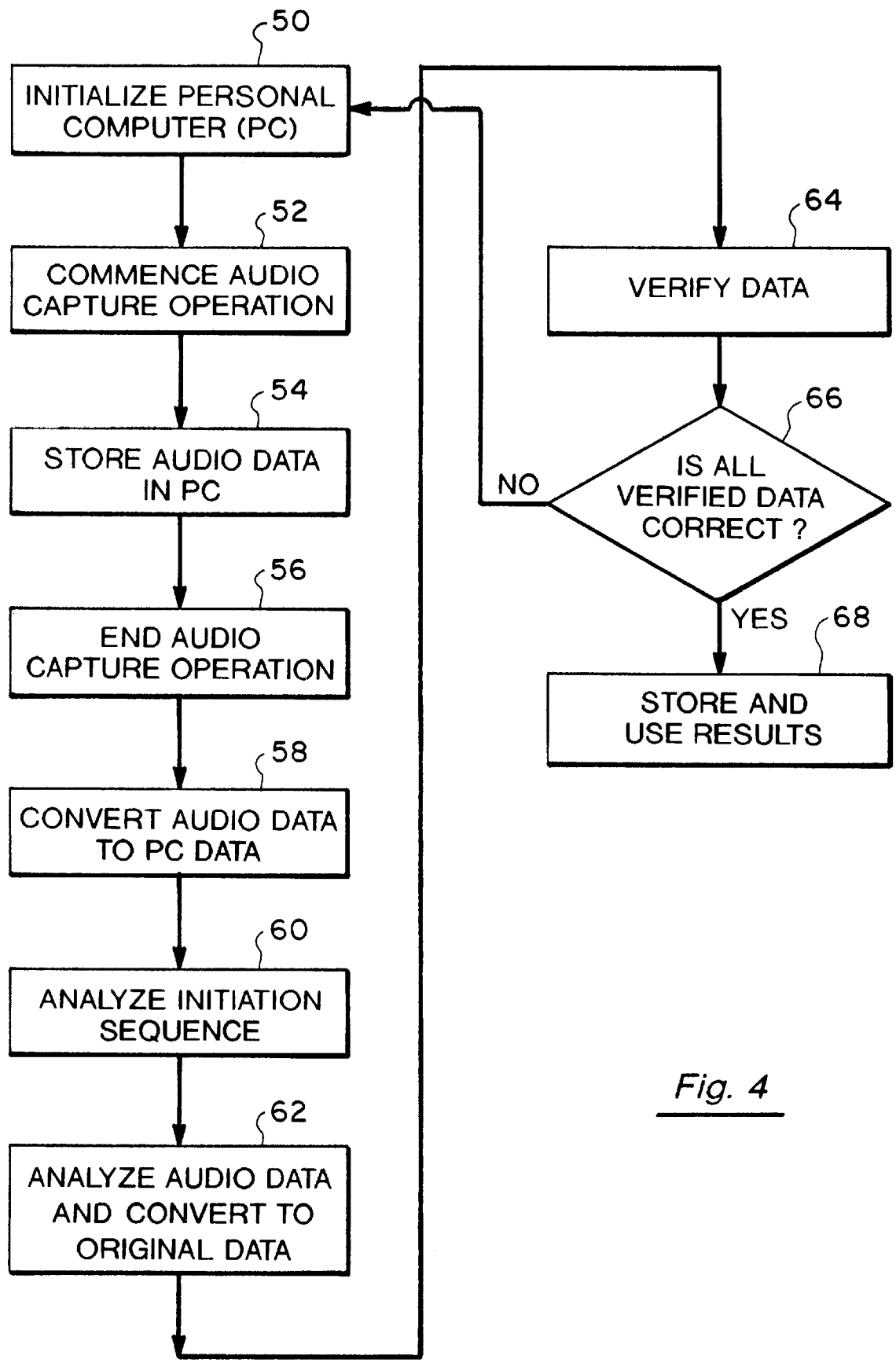
FIG. 4 is a flow diagram of the data process at the personal computer.

Referring now to FIG. 4, the personal computer 16 is programmed for response to the source. At flow stage 50, the personal computer is first initialized to prepare for capture of transmitted audio energy from the source. The user may execute a program on the PC which controls the audio hardware 18 (FIG. 1) and necessary setup commands are executed in preparation for receiving the audio waveforms. The sampling rate, input channel allocation and gain settings are all established. Flow stage 52 sees commencement of the audio capture operation as the user employs a mouse or keyboard to issue a command to the program that is running on the PC to begin audio capture operation. The PC program is set up to instruct the audio hardware 18 to initiate a continuous audio capture mode and this continuous mode will remain in effect until the user instructs the program to terminate the mode, or until the program terminates under control of its resident logic.

After transmission begins from the source, and the download function has commenced, the audio information captured by the audio hardware is retained either in random access memory or as a file on disk by the PC program as indicated at flow step 54. This data will then be available to the PC program during the next step, that of conversion or demodulation of the audio information to binary data. Thus, if the audio hardware was in capture mode for ten seconds, and it was sampling at a rate of 5 Khz with a resolution of 8 bits (one byte) per sample, the program would have a resulting temporary file size of 10 times 5000 bytes, or 50,000 bytes.

The flow stage 56 functions to end the audio capture operation. After all data transmission has been accomplished, the continuous audio capture mode is terminated and the PC program resets the audio hardware to an idle state. At flow stage 58, the PC program logic analyzes the captured, digitized audio file to identify the waveform representations of specific bits, and to collect them into an exact re-creation of the original data as it was stored in the source or timepiece.

The PC program scans the digitized audio file progressively from the beginning in flow stage 60 until it finds the waveform representation of the designated initiation sequence. During the development of the source programming, the exact initiation sequence was specified and is therefore recognizable by the PC program. By identifying the sequence of bits, the PC program determines facts required for the further analysis of the audio file. The scan finds the starting point of the data which is a specified time after the initiation sequence. The scan then determines the number of samples that are taken for a single bit representation. For example, if the original initiation sequence was "1010", the program may identify it as 50 samples of tone, followed by 50 samples of silence, 50 of tone, and 50 of silence. This will then establish that each data bit in the remainder of the file will also be represented by 50 samples.

Flow stage 62 then functions to analyze the audio data and convert to original data. The PC program scans the remainder of the audio file and, using the decoding information extracted from the initiation sequence, analyzes the information to derive the stream of individual data bits ("1"s and "0"s). The individual data bits are then converted to bytes of data according to the sending protocol that was used for the audible transmission. For example, if bytes are transmitted MSB first and each bit is 50 samples, a series of eight 50-sample segments can reconstruct a byte of the original transmitted data. If continuous waveform (CW) encoding is used, each 50-sample segment is evaluated to determine if a tone is present. If so, the bit is then a 1, otherwise it is a "0". All segments in the file may be evaluated in this manner until all are converted to data bits and full bytes of data are reconstructed.

At flow stage 64, an optional step compares the retrieved data with an n-byte checksum or similar mechanism that is sent after the last byte of actual data. If the transmitted data does not verify correct, this will be determined in flow stage 66 whereupon a negative response causes flow to revert to the flow stage 50 for re-initialization of the personal computer thereby to restart the entire process from the beginning of download. If verification is affirmative at decision stage 66, flow is via the affirmative branch to flow stage 68 where the result of the download is stored as data in a file; or, incorporated into a data base or any application software or data storage scheme.

In operation, the audio transmission system may be employed variously for the purpose of gathering data. A source or timepiece might be used by a runner in training to gather performance data for later transmission playback into a central computer for analysis and recording. Alternatively, a data source may be carried by other data collectors such as a meter reader or a scientist gathering data at a remote site. In any event, once the data gathering is complete, it is only necessary to proceed to the central computer location or home base to complete the data down-loading and evaluation steps.

The foregoing discloses a novel system for recording physical activity data during the activity so that the data can be later downloaded to a central computer for the purpose of analysis, graphic display, print out, and entry into permanent records for future comparison. Certain readily constructed data is especially valuable for a runner in training because he is able to maintain continual comparison of specific data accomplishments thereby to establish improvement over a period of time. The runner is able to record not only the speed-related parameters such as distance times, limited lap times, and beginning and ending speed rates, but also such physical activity as pulse/heart rate and other sensed physical condition data.

Changes may be made in the combination and arrangement of elements as heretofore set forth in the specification and shown in the drawings; it being understood that changes may be made in the embodiments disclosed without departing from the spirit and scope of the invention as defined in the following claims.

What is claimed is:

1. A system for recording predetermined personal data relating to a user and subsequently transmitting the personal data to an external computer having means for receiving and processing coded audio tones, said system comprising:
   a time piece having at least one timing function when carried by the user;
   a memory functioning in coaction with said time piece;
   means sensing selected personal data and storing said personal data in said memory; and
   audible means communicating with said memory for subsequently transmitting the stored personal data as coded audio tones to the external computer.

2. The system of claim 1 wherein said audible means comprise a piezoelectric element.

3. The system of claim 1 wherein said time piece comprises a wristwatch.

4. The system of claim 1 wherein said personal data comprises data regarding the user's heart rate.

5. The system of claim 1 wherein said personal data comprises ECG data for the user.

6. The system of claim 1 wherein said coded audio tones are modulated using continuous wave modulation.

7. The system of claim 1 wherein said coded audio tones are modulated using frequency shift keying modulation.

8. A method for storing and evaluating predetermined personal data relating to a user during an activity, comprising:

providing the user with a time piece;

recording predetermined personal data during the user's activity to produce a stored indication in said time piece;

playing back said stored indication in the form of coded audio tones after the sure's activity;

receiving said coded audio tones for input to a computer; and processing the coded audio tones to analyze said personal to data.

9. A method of claim 8 wherein said coded audio tones are generated by a piezoelectric element.

10. The method of claim 8 wherein said time piece comprises a wristwatch.

11. The method of claim 8 wherein said personal data comprises data regarding the user's heart rate.

12. The method of claim 8 wherein said personal data comprises ECG data for the user.

13. The method of claim 8 wherein said coded audio tones are modulated using continuous wave modulation.

14. The method of claim 8 wherein said coded audio tones are modulated using frequency shift keying modulation.

\* \* \* \* \*